(12) United States Patent
Tatum, Jr. et al.

(10) Patent No.: US 9,861,455 B2
(45) Date of Patent: Jan. 9, 2018

(54) DENTAL IMPLANT SYSTEM

(71) Applicant: TI Intellectual Property Inc., Tortola (BV)

(72) Inventors: O Hilt Tatum, Jr., St. Etienne du Vauvray (FR); Anthony Fiorello, III, Palm Harbor, FL (US)

( * ) Notice: Subject to any disclaimer, the term of this patent is extended or adjusted under 35 U.S.C. 154(b) by 218 days.

(21) Appl. No.: 14/446,251

(22) Filed: Jul. 29, 2014

(65) Prior Publication Data

US 2015/0037758 A1    Feb. 5, 2015

Related U.S. Application Data

(60) Provisional application No. 61/859,862, filed on Jul. 30, 2013.

(51) Int. Cl.
*A61C 8/00* (2006.01)

(52) U.S. Cl.
CPC ............. *A61C 8/006* (2013.01); *A61C 8/008* (2013.01); *A61C 8/0022* (2013.01); *A61C 8/0068* (2013.01); *A61C 8/0089* (2013.01); *A61C 2008/0046* (2013.01)

(58) Field of Classification Search
CPC ..... A61C 8/006; A61C 8/0068; A61C 8/0022; A61C 8/008; A61C 2008/0046
USPC .................................................. 433/173, 174
See application file for complete search history.

(56) References Cited

U.S. PATENT DOCUMENTS

| | | | |
|---|---|---|---|
| 3,974,001 A | 8/1976 | Steinmann et al. | |
| 4,040,129 A | 8/1977 | Steinmann et al. | |
| 4,114,423 A | 9/1978 | Wenger | |
| 4,115,156 A | 9/1978 | Straumann | |
| 4,147,568 A | 4/1979 | Marechal | |
| 4,177,669 A | 12/1979 | Wenger | |
| 4,180,910 A | 1/1980 | Straumann et al. | |
| 4,219,015 A | 8/1980 | Steinmann | |
| 4,320,875 A | 3/1982 | Sutter | |
| 4,328,593 A | 5/1982 | Sutter et al. | |
| 4,332,036 A | 6/1982 | Sutter et al. | |
| 4,388,921 A | 6/1983 | Sutter et al. | |
| 4,431,416 A | 2/1984 | Niznick | |
| 4,447,209 A | 5/1984 | Sutter | |
| 4,488,875 A | 12/1984 | Niznick | |
| 4,553,942 A | 11/1985 | Sutter | |
| 4,640,983 A | 2/1987 | Comte | |
| 4,645,453 A | 2/1987 | Niznick | |
| 4,713,003 A * | 12/1987 | Symington | A61C 8/0022 433/173 |
| 4,758,161 A | 7/1988 | Niznick | |
| 4,781,072 A | 11/1988 | Tschudin | |
| 4,945,342 A | 7/1990 | Steinemann | |
| 4,960,381 A | 10/1990 | Niznick | |

(Continued)

*Primary Examiner* — Pedro Philogene
*Assistant Examiner* — David C Comstock
(74) *Attorney, Agent, or Firm* — Frijouf, Rust & Pyle, P.A.

(57) ABSTRACT

An improved dental system is disclosed for implanting into a jawbone of a patent comprising a dental implant having a coronal end and a small apical end with an orifice extending from the coronal end toward the apical end. An orientation portion is disposed in the orifice for aligning an abutment relative to the dental implant. A threaded portion is disposed in the orifice for receiving a threaded portion of the abutment for securing the abutment to the dental implant. Preferably, the orifice extends at least one-half the length of the dental implant.

16 Claims, 12 Drawing Sheets

(56) References Cited

U.S. PATENT DOCUMENTS

| | | |
|---|---|---|
| 4,983,184 A | 1/1991 | Steinemann |
| 5,030,095 A | 7/1991 | Niznick |
| 5,061,181 A | 10/1991 | Niznick |
| 5,062,800 A | 11/1991 | Niznick |
| 5,071,350 A | 12/1991 | Niznick |
| 5,076,788 A | 12/1991 | Niznick |
| RE33,796 E | 1/1992 | Niznick |
| 5,078,607 A | 1/1992 | Niznick |
| 5,087,605 A | 2/1992 | Hegde et al. |
| 5,196,016 A | 3/1993 | Buser et al. |
| 5,281,140 A | 1/1994 | Niznick |
| 5,306,149 A | 4/1994 | Schmid et al. |
| 5,334,024 A | 8/1994 | Niznick |
| 5,368,483 A | 11/1994 | Sutter et al. |
| 5,427,527 A | 6/1995 | Niznick et al. |
| 5,433,606 A | 7/1995 | Niznick |
| 5,433,607 A | 7/1995 | Schmid et al. |
| 5,456,723 A | 10/1995 | Steinemann et al. |
| 5,571,017 A | 11/1996 | Niznick |
| 5,575,650 A | 11/1996 | Niznick et al. |
| 5,584,629 A | 12/1996 | Bailey et al. |
| 5,605,457 A | 2/1997 | Bailey et al. |
| 5,607,304 A | 3/1997 | Bailey et al. |
| 5,622,500 A | 4/1997 | Niznick |
| 5,626,227 A | 5/1997 | Wagner et al. |
| 5,628,630 A | 5/1997 | Misch et al. |
| 5,660,545 A | 8/1997 | Bailey et al. |
| 5,667,384 A | 9/1997 | Sutter et al. |
| 5,734,113 A | 3/1998 | Vogt et al. |
| 5,755,807 A | 5/1998 | Anstaett et al. |
| 5,782,918 A | 7/1998 | Klardie et al. |
| 5,823,777 A | 10/1998 | Misch et al. |
| 5,836,768 A | 11/1998 | Huskens et al. |
| 5,882,200 A | 3/1999 | Sutter et al. |
| 5,885,079 A | 3/1999 | Niznick |
| 5,888,218 A | 3/1999 | Folsom |
| 5,927,979 A | 7/1999 | Misch et al. |
| 5,947,733 A | 9/1999 | Sutter et al. |
| 5,954,504 A | 9/1999 | Misch et al. |
| 5,989,028 A | 11/1999 | Niznick |
| 6,045,361 A | 4/2000 | Misch et al. |
| 6,068,478 A | 5/2000 | Grande et al. |
| 6,068,480 A | 5/2000 | Misch et al. |
| 6,083,004 A | 7/2000 | Misch et al. |
| 6,102,702 A | 8/2000 | Folcom, Jr. et al. |
| 6,120,292 A | 9/2000 | Buser et al. |
| 6,244,867 B1 | 6/2001 | Aravena et al. |
| 6,261,097 B1 | 7/2001 | Schmutz et al. |
| 6,287,117 B1 | 9/2001 | Niznick |
| 6,402,759 B1 | 6/2002 | Strong et al. |
| 6,419,491 B1 | 7/2002 | Ricci et al. |
| 6,454,569 B1 | 9/2002 | Hollander et al. |
| 6,663,388 B1 | 12/2003 | Svhar et al. |
| 6,702,855 B1 | 3/2004 | Steinemann et al. |
| 6,726,480 B1 | 4/2004 | Sutter |
| 6,830,573 B2 | 12/2004 | Strong et al. |
| 6,863,529 B2 | 3/2005 | Strong et al. |
| 7,014,464 B2 | 3/2006 | Niznick |
| 7,087,085 B2 | 8/2006 | Steinemann et al. |
| 7,108,510 B2 | 9/2006 | Niznick |
| 7,207,801 B2 | 4/2007 | Vogt et al. |
| 7,282,584 B2 | 10/2007 | Molenberg |
| 7,300,284 B2 | 11/2007 | Linder |
| 7,322,956 B2 | 1/2008 | Fehr et al. |
| 7,329,124 B2 | 2/2008 | Mundwiler et al. |
| 7,337,896 B2 | 3/2008 | Brunner |
| 7,396,231 B2 | 7/2008 | Niznick |
| 7,423,013 B2 | 9/2008 | Lyngstadaas et al. |
| D578,218 S | 10/2008 | Purga et al. |
| D582,042 S | 12/2008 | Purga et al. |
| D587,371 S | 2/2009 | Purga et al. |
| 7,559,765 B2 | 7/2009 | Courvoisier |
| D587,372 S | 9/2009 | Purga et al. |
| D587,373 S | 9/2009 | Purga et al. |
| 7,608,284 B2 | 10/2009 | Gestrelius et al. |
| 7,623,693 B2 | 11/2009 | Holzner et al. |
| 7,654,824 B2 | 2/2010 | Ebi et al. |
| 7,662,190 B2 | 2/2010 | Steinemann et al. |
| 7,665,990 B2 | 2/2010 | Mundwiler et al. |
| 7,667,891 B2 | 2/2010 | Cok et al. |
| 7,689,308 B2 | 3/2010 | Holzner et al. |
| 7,694,812 B2 | 4/2010 | Bammerlin et al. |
| 7,695,279 B2 | 4/2010 | Hirsch et al. |
| 7,699,613 B2 | 4/2010 | Niznick |
| 7,718,100 B2 | 5/2010 | Soler et al. |
| 7,721,890 B2 | 5/2010 | Neidhardt |
| 7,741,427 B2 | 6/2010 | Molenberg |
| 7,774,080 B2 | 8/2010 | Holzner et al. |
| 7,785,107 B2 | 8/2010 | Niznick |
| 7,827,694 B2 | 11/2010 | Soler et al. |
| 8,118,596 B2 | 2/2012 | Niznick |
| 2003/0194679 A1* | 10/2003 | Odrich .................. A61C 8/005 433/173 |
| 2006/0199150 A1 | 9/2006 | Niznick |
| 2009/0239196 A1* | 9/2009 | Lerner .................. A61C 8/005 433/174 |
| 2010/0151421 A1* | 6/2010 | Devengencie ......... A61C 8/005 433/174 |

* cited by examiner

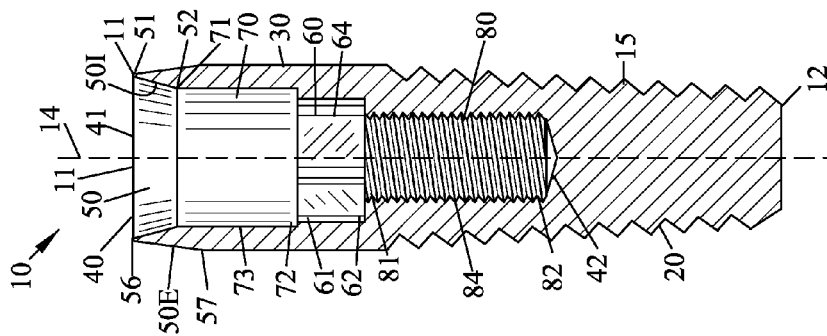
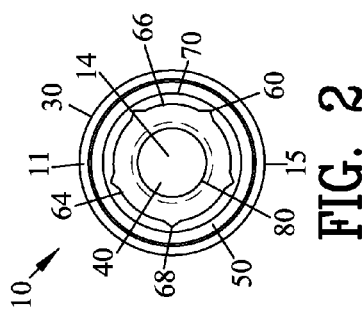
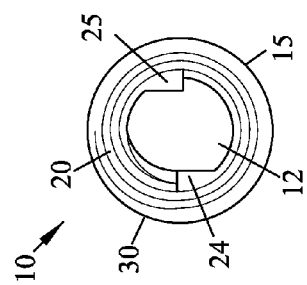
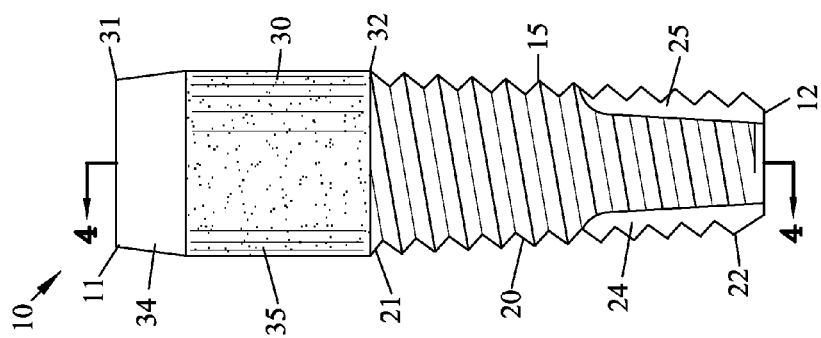

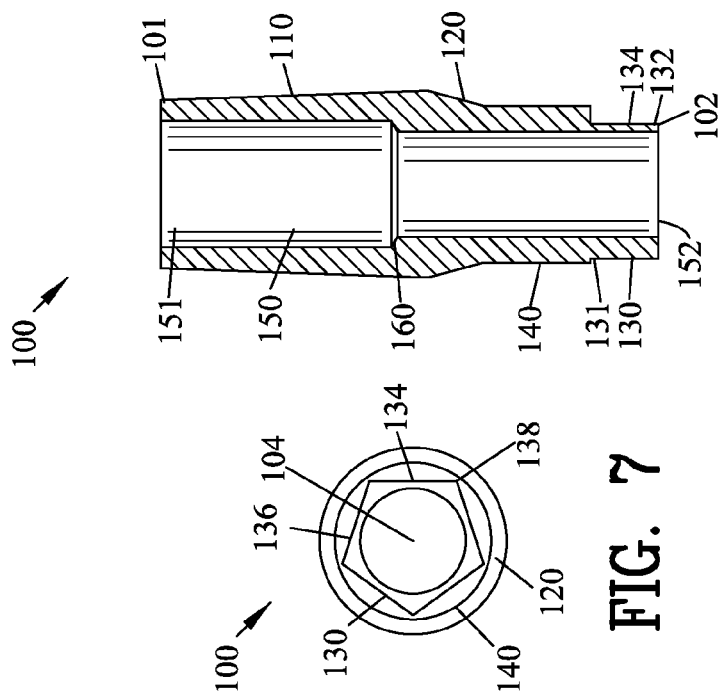

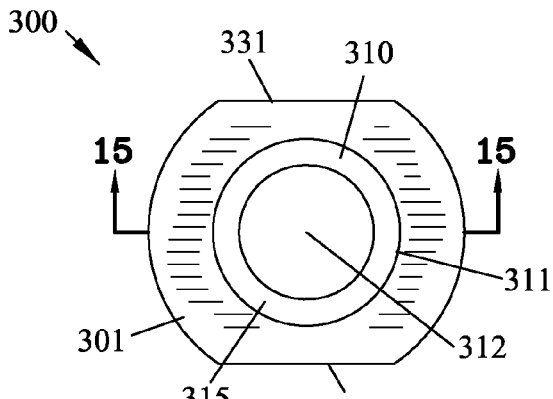
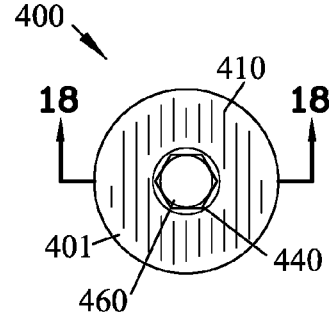
FIG. 14
FIG. 17
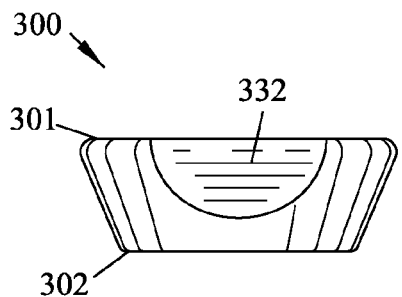
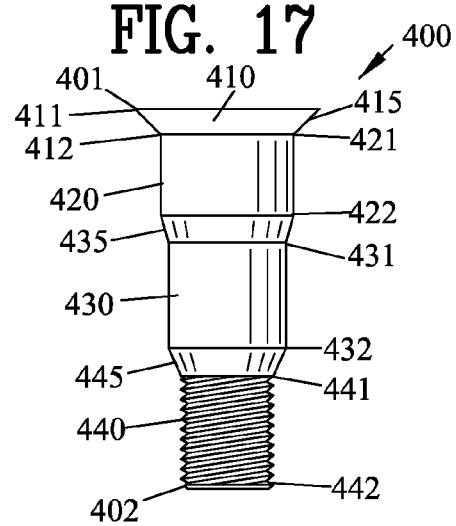
FIG. 13
FIG. 16
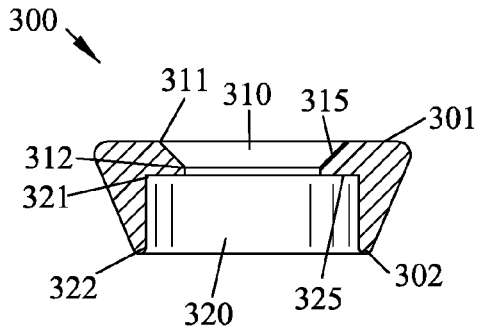
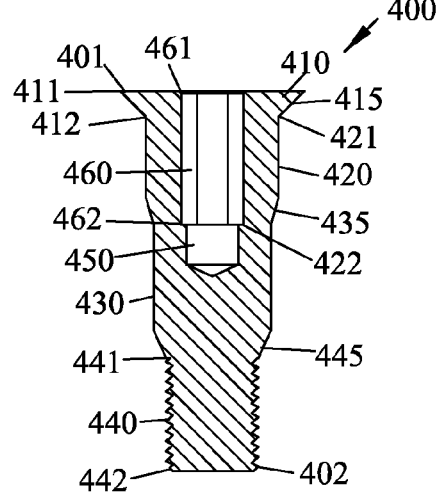
FIG. 15
FIG. 18

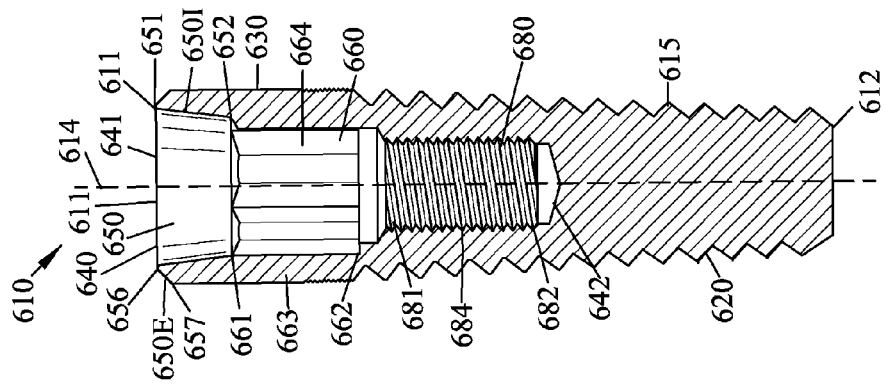
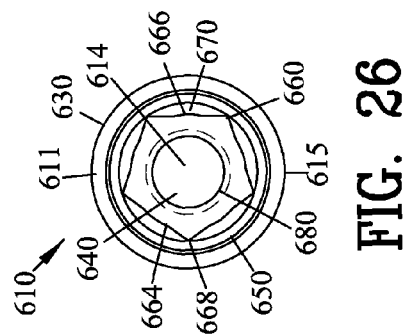
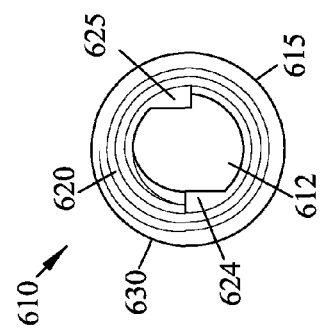
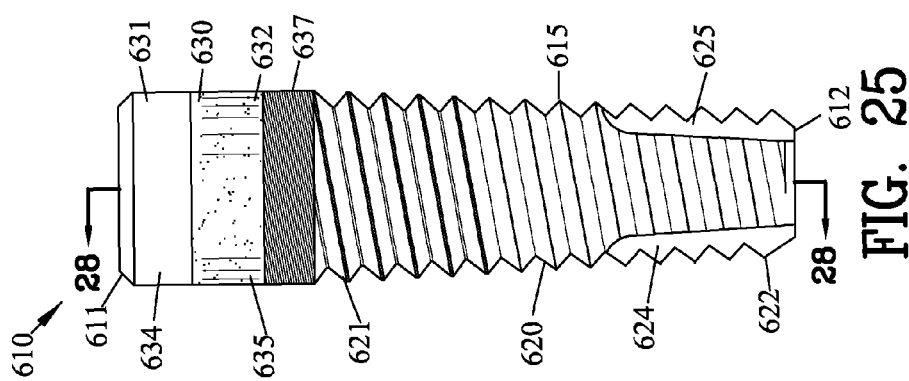

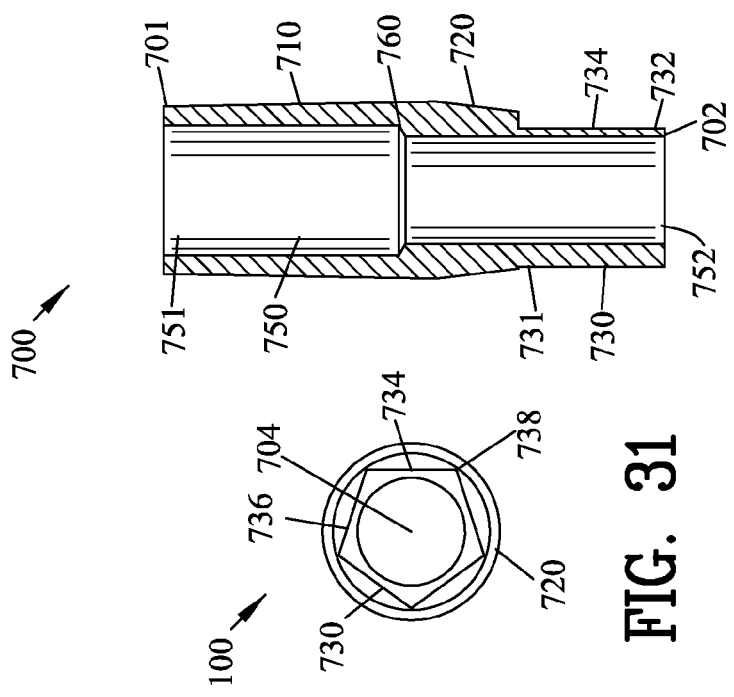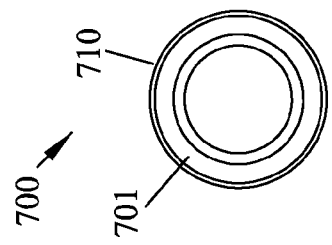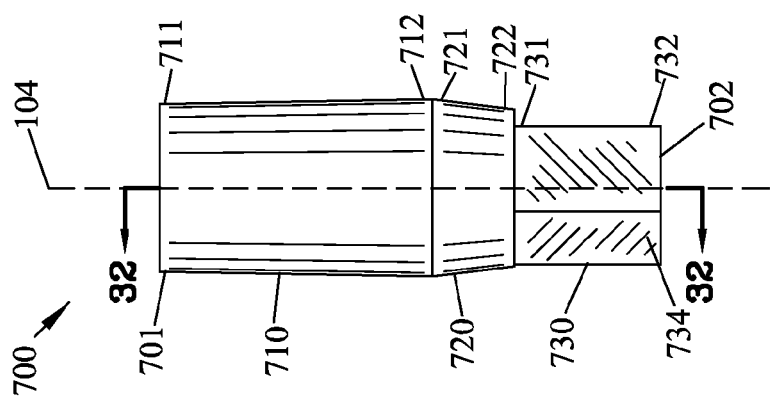

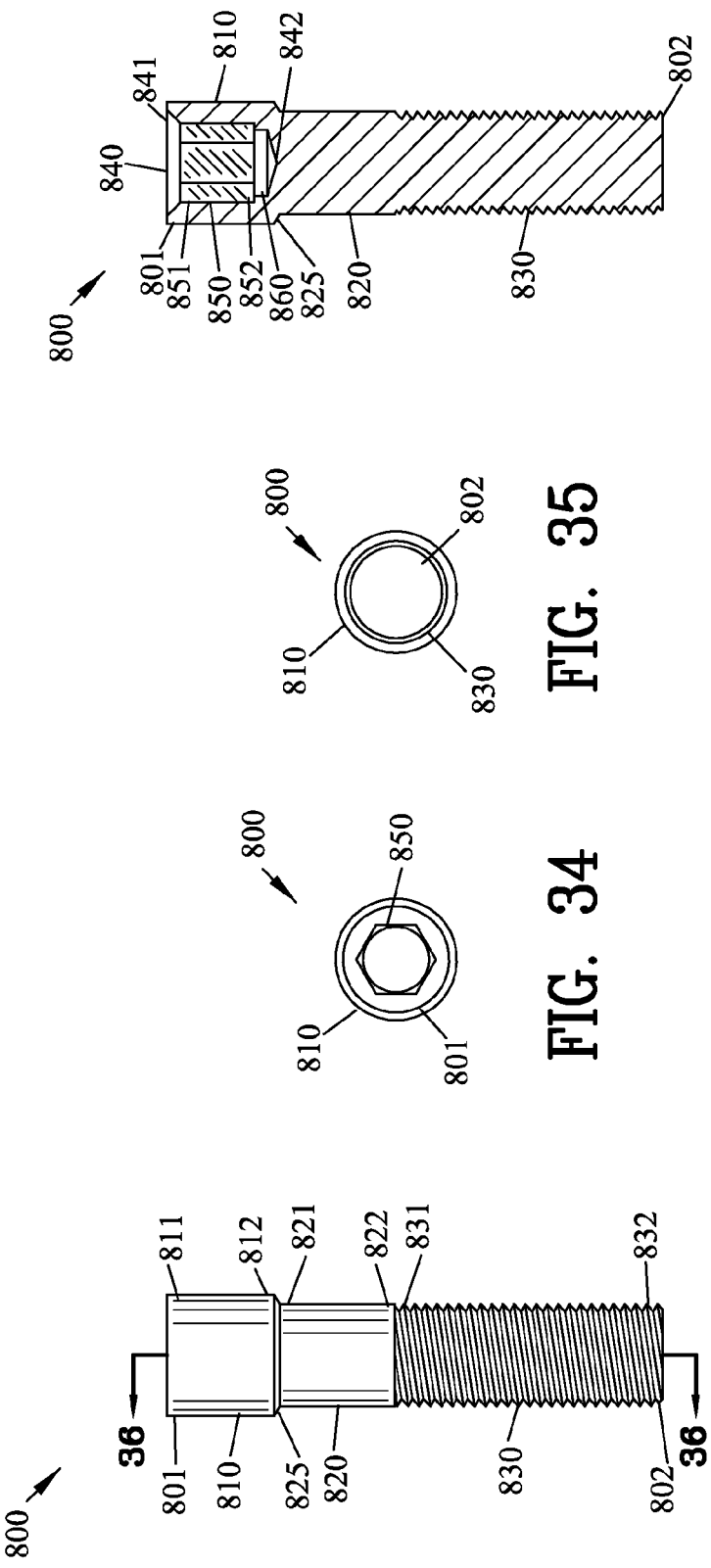

DENTAL IMPLANT SYSTEM

CROSS-REFERENCE TO RELATED APPLICATIONS

This application claims benefit of U.S. Patent provisional application No. 61/859,862 filed 30 Jul. 2013. All subject matter set forth in provisional application No. 61/859,862 filed 30 Jul. 2013 is hereby incorporated by reference into the present application as if fully set forth herein.

BACKGROUND OF THE INVENTION

Field of the Invention

This invention relates to dentistry and more particularly to an improved dental system for implantation into a jawbone of a patient.

Description of the Related Art

Various types of endosseous dental implants have been developed over the years. Improved materials and techniques have increase the use and popularity of endosseous dental implants in recent years. The advent of the root-form endosseous dental implant has made the implantation procedure easier for the implant specialist.

The most popular root-form endosseous dental implant is the screw type root-form endosseous dental implant. The screw type root-form endosseous dental implant incorporates external threads on the implant for engaging with the jaw bone of the patient. Many implant specialist use automatic torque devices for screwing the screw type dental implant into the jaw bone of the patient.

Although the root-form endosseous dental implants have contributed to the dental health of the public, many of these dental implants fail due to the forces exerted upon the dental implant through normal mastication. Among the most frequent failures is the fracture of the abutment due to lateral forces being applied to a dental crown. These failures are comparable to an occurrence commonly referred to as an "ice cream cone affect". Many children have unfortunate experience of ice cream rolling off the top of an ice cream cone due to lateral forces being applied to the ice cream. Similarly, many abutments have failed due to improper mounting within the dental implant.

Therefore, it is an object of the present invention to provide an improved dental implant that overcomes the deficiencies of the dental implants of the prior art.

Another object of this invention is to provide an improved dental implant with superior strength to reduce the possibility of an implant failure.

Another object of this invention is to provide an improved dental implant incorporating a new interface between a dental implant and an abutment for supporting a dental crown.

Another object of this invention is to provide an improved dental implant with superior lateral stability.

Another object of this invention is to provide an improved dental implant with superior strength heretofore unknown in the dental art.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved dental prosthesis for implanting into a jawbone of a patient and for mounting an abutment comprising a dental implant having a coronal end and a small apical end. An orifice extends into the dental implant from an external orifice end adjacent to the coronal end toward an internal orifice end in proximity to the apical end. A threaded portion is disposed in the orifice located adjacent to the internal end of the orifice. An orientation portion is disposed in the orifice located in proximity to the coronal end of the dental implant. A keyway is defined in the orientation portion for receiving a corresponding key defined in the abutment for aligning the abutment relative to the dental implant. A threaded screw engages with the threaded portion in the orifice for securing the abutment to the dental implant.

In a more specific example of the invention, the dental implant has an outer surface reducing in diameter from the coronal end to the apical end. An outer surface of the dental implant defines outer threads for affixing the dental implant to the jawbone of a patient. The external end adjacent to the coronal end is an open end and the internal end in proximity to the apical end is a closed end.

Preferably, a taper portion is defined in the orifice immediately adjacent to the coronal end. An inner taper portion is defined in the orifice immediately adjacent to the coronal end. The inner taper portion defines a taper angle of approximately seven degrees relative to an axis of symmetry extending through the dental implant. An external taper portion is immediately adjacent to the coronal end. The external taper portion defines a taper angle of approximately forty-five degrees relative to an axis of symmetry extending through the dental implant.

In a more specific example of the invention, the keyway includes a pentagonal keyway for receiving a pentagonal keyed tool for screwing the dental implant into the jaw bone of the patient. The keyway includes a pentagonal keyway for aligning the abutment relative to the dental implant.

In one example of the invention, the dental implant includes a counter bore disposed in the orifice and interposed between the orientation portion and the threaded portion for providing increased lateral stability to the abutment. The counter bore defines a cylindrical counter bore for receiving a cylindrical portion of the abutment. The cylindrical counter bore has a diameter greater that the diameter of the threaded portion. The counter bore provides increased lateral stability to the abutment.

In another example of the invention, the invention is incorporated into an improved dental prosthesis for implanting into a jawbone of a patient and for mounting an abutment. The improved dental prosthesis comprises a dental implant having a coronal end and a small apical end. An orifice extends into the dental implant from an external orifice end adjacent to the coronal end toward an internal orifice end in proximity to the apical end. An orientation portion is located in the orifice for aligning the abutment relative to the dental implant. A threaded portion is disposed in the orifice adjacent to the apical end of the dental implant. The orifice extends at least one-half the distance from the coronal end to the apical In still another example of the invention, the invention is incorporated into an improved dental prosthesis for implanting into a jawbone of a patient. The improved dental prosthesis comprises a dental implant having a coronal end and a small apical end. An orifice extends into the dental implant from an external orifice end adjacent to the coronal end toward an internal orifice end in proximity to the apical end. A threaded portion is disposed in the orifice located adjacent to the internal end of the orifice. An orientation portion is disposed in the orifice located in proximity to the coronal end of the dental implant. A keyway is defined in the orientation portion for receiving a corresponding key defined in the abutment for aligning the abutment relative to the dental implant. An abutment mounts a dental fixture. A key is defined in the abutment for insertion into the keyway defined in the orientation portion for aligning the abutment relative to the dental implant. A threaded screw engages with the threaded portion in the orifice for securing the abutment to the dental implant.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 1 is a side view of a dental implant incorporating the present invention;
FIG. 2 is a top view of FIG. 1;
FIG. 3 is a bottom view of FIG. 1;
FIG. 4 is a sectional view along 4-4 in FIG. 1;
FIG. 5 is a side view of an abutment suitable for use with dental implant of FIG. 1;
FIG. 6 is a top view of FIG. 5;
FIG. 7 is a bottom view of FIG. 5;
FIG. 8 is a sectional view along 8-8 in FIG. 5;
FIG. 13 is a side view of a healing cuff suitable for use with dental implant of FIG. 1;
FIG. 14 is a top view of FIG. 13;
FIG. 15 is a sectional view along 15-15 in FIG. 14;
FIG. 16 is a side view of a healing cuff screw suitable for use with dental implant of FIG. 1;
FIG. 17 is a top view of FIG. 16;
FIG. 18 is a sectional view along 18-18 in FIG. 17;
FIG. 25 is a side view of a dental implant incorporating the present invention;
FIG. 26 is a top view of FIG. 25;
FIG. 27 is a bottom view of FIG. 25;
FIG. 28 is a sectional view along 28-28 in FIG. 25;
FIG. 29 is a side view of an abutment suitable for use with dental implant of FIG. 25;
FIG. 30 is a top view of FIG. 29;
FIG. 31 is a bottom view of FIG. 29;
FIG. 32 is a sectional view along 32-32 in FIG. 29;
FIG. 33 is a side view of an abutment screw suitable for use with dental implant of FIG. 25;
FIG. 34 is a top view of FIG. 33;
FIG. 35 is a bottom view of FIG. 33;
FIG. 36 is a sectional view along 36-36 in FIG. 33.

DETAILED DISCUSSION

Figure 12:
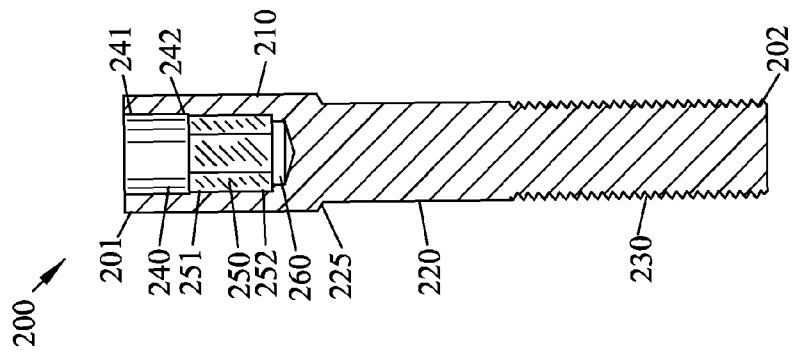
FIG. 12 is a sectional view along 12-12 in FIG. 9.
Figure 11:
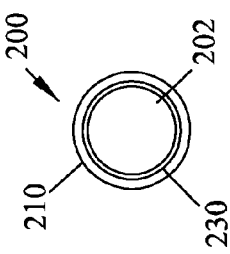
FIG. 11 is a bottom view of FIG. 9.
Figure 10:
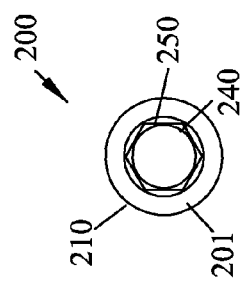
FIG. 10 is a top view of FIG. 9.
Figure 9:
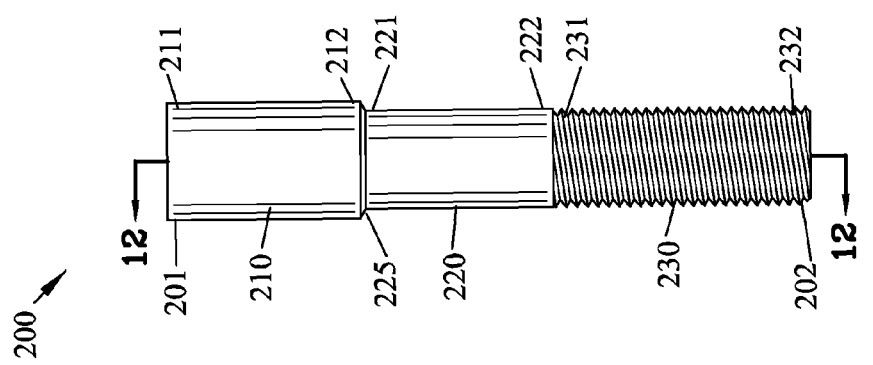
FIG. 9 is a side view of an abutment screw suitable for use with dental implant of FIG. 1.

FIGS. 1-5 are various views of a dental implant 10 incorporating the present invention. Preferably, the dental implant 10 is used in concert with an abutment 100 shown in FIGS. 6-8, an abutment screw 200 shown in FIGS. 9-12 along with a healing cuff 300 and healing cuff screw shown in FIG. 1318

The dental implant 10 extends between a coronal end 11 and an apical end 12 defining an axis of symmetry 14. The dental implant 10 has an outer surface 15 reducing in diameter from the coronal end 11 to the apical end 12. The outer surface 15 of the dental implant 10 defines an outer thread segment 20 extending between a first end 21 and a second end 22. The outer thread segment 20 defines opposed cutouts 24 and 25 for providing a self tapping lead in for the thread segment 20. As will be described in greater detail hereinafter, the outer thread segment 20 affixes the dental implant 10 to a jawbone of a patient.

The dental implant 10 has cylindrical segment 30 extending between a first and a second end 31 and 32 located in proximity to the coronal end 11. The cylindrical segment 30 comprises an upper cylindrical segment 34 and a lower cylindrical segment 35. Preferably, threaded segment 20 and the lower cylindrical segment 35 are treated with an abrasive material to provide a rough surface for adhering to a jawbone of a patient as will be described in greater detail hereinafter.

An orifice 40 extends into the dental implant 10 from an external orifice end 41 adjacent to the coronal end 11 toward an internal orifice end 42 in proximity to the apical end 12. The external end 41 adjacent to the coronal end 11 is an open end whereas the internal end 42 is a closed end.

A taper portion 50 is defined in the orifice 40 immediately adjacent to the coronal end 11. The taper portion 50 includes an inner taper portion 501 and an external taper portion 50E. The inner taper portion 501 extends between a first and a second taper end 51 and 52. The inner taper portion 501 defines a taper angle of fifteen degrees (15°) relative to the axis of symmetry 14 extending through the dental implant 10.

The external taper portion 50E is defined in an outer surface of the cylindrical segment 30 adjacent to the first end 31. The external taper portion 50E extends between a first and a second taper end 56 and 57. The external taper portion 50E defines a taper angle of four degrees (4°) relative to the axis of symmetry 14 extending through the dental implant 10.

An orientation portion 60 is disposed in the orifice 40 located immediately adjacent to the taper portion 50 and in proximity to the coronal end 11 of the dental implant 10. The orientation portion 60 extends between a first and a second orientation end 61 and 62. A keyway 64 is defined in the orientation portion 60 for receiving a corresponding key defined in the abutment 100 for aligning the abutment 100 relative to the dental implant 10.

As best shown in FIG. 2, the keyway 64 is shown as a pentagon keyway defining a minimum radius 66 a maximum radius 68 relative to the axis of symmetry 14. The pentagon keyway 64 enables alignment of the abutment 100 in five different orientations relative to the dental implant 10. In addition, the keyway 64 provides a socket for receiving a conventional pentagon keyed tool (not shown) for screwing the dental implant 10 into the jaw bone of the patient.

A counter bore 70 disposed in the orifice 40 adjacent to a threaded portion 80. The counter bore 70 extends between a first and a second counter bore end 71 and 72. As will be described in greater detail hereinafter, the counter bore 70 defines a cylindrical wall 73 for receiving a corresponding cylindrical portion of the abutment 100.

A threaded portion 80 is disposed in the orifice 40 between the orientation portion 60 and the internal end 42 of the orifice 40. The threaded portion 80 extends between a first and a second end 81 and 82 defining threads 84. The threaded portion 80 receives a corresponding threaded portion of the abutment screw 200 for securing the abutment 100 to the dental implant 10.

The cylindrical counter bore 70 has a diameter greater than the diameter of the threaded portion 80. The larger diameter cylindrical counter bore 70 enables a threaded portion of an abutment screw 200 to pass through the counter bore 70 and engage with the threaded portion 80 of the dental implant 10. Furthermore, the cylindrical counter bore 70 has a diameter commensurate with the keyway maximum radius 68 of the keyway 60.

An important aspect of the present invention is the length of the orifice 40 relative to the length of the dental implant 10. The length of the orifice 40 between the external orifice end 41 and the internal orifice end 42 represents a major portion of the distance between the coronal end 11 and the apical end 12 of the dental implant 10. The length of the orifice 40 provides increased lateral stability to the abutment 100 as will be described with reference to FIGS. 22 and 23.

Figure 23:
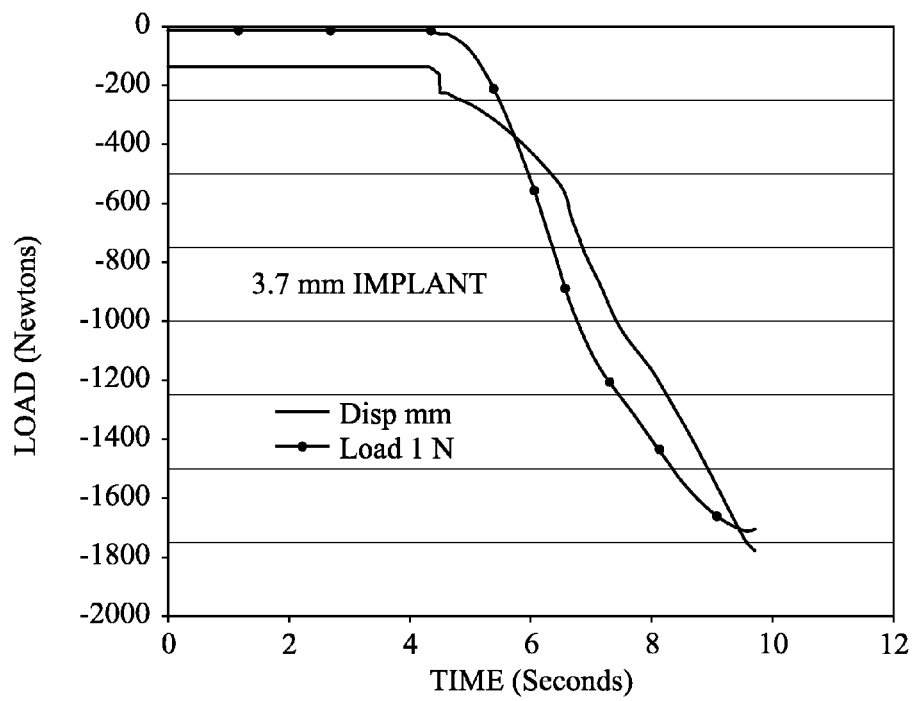
FIG. 23 is a graph of force applied to the dental implant of the present invention as a function of time illustrating the strength of a 3.7 mm dental implant.

FIGS. 5-8 are various views of an abutment 100 suitable for use with dental implant 10 of FIG. 1. The abutment 100 extends between a first end 101 and a second end 102 along an axis of symmetry 104. The abutment 100 has mounting segment 110 extending between a first and a second end 111 and 112 located in proximity to the first end 101 of the abutment 100. The mounting segment 110 is adapted to receive a dental crown as shown in FIG. 23.

A taper segment 120 is located immediately adjacent to the mounting segment 110. The taper segment 120 extends between a first and a second taper end 121 and 122. The taper segment 120 defines a taper angle corresponding to the taper portion 50 disposed in the orifice 40 of the dental implant 10.

An orientation segment 130 is located immediately adjacent to the cylindrical segment 140. The orientation segment 130 extends between a first and a second orientation end 131 and 132. A key 134 is defined in the orientation segment 130 for insertion into the corresponding keyway 64 defined in the dental implant 10 for aligning the abutment 100 relative to the dental implant 10.

As best shown in FIG. 7, the key 134 is shown as a pentagon key defining a minimum radius 136 a maximum radius 138 relative to the axis of symmetry 104. The pentagon key 134 enables alignment of the abutment 100 in five different orientations relative to the dental implant 10.

A cylindrical segment 140 is located immediately adjacent to the orientation segment 130. The cylindrical segment 140 extends between a first and a second cylindrical end 141 and 142. The cylindrical segment 140 defines cylindrical wall 143 for receipt within the counter bore 70 of the dental implant 10.

An abutment bore 150 extends through the abutment 100 from a first bore end 151 and a second bore end 152. An abutment shoulder 160 extends into the abutment bore 150 intermediate the first and second bore ends 151 and 152. As will be described in greater detail hereinafter, the abutment shoulder 160 is angled to receive and engage with the abutment screw 200 for securing the abutment 100 to the dental implant 10.

FIGS. 9-12 are various views of the abutment screw 200 suitable for use with dental implant 10 of FIGS. 1-4 and the abutment 100 of FIGS. 5-8. The abutment screw 200 extends between a first and a second abutment screw end 201 and 202.

The abutment screw 200 has an upper abutment screw segment 210 extending between a first and a second end 211 and 212 located in proximity to the first abutment screw end 201 of the abutment screw 200. The upper abutment screw segment 210 is adapted to be received within the abutment bore 150 of the abutment 100.

The abutment screw 200 has a lower abutment screw segment 220 extending between a first and a second end 221 and 222. An abutment screw shoulder 225 is interposed between the upper abutment screw segment 210 and the lower abutment screw segment 220. The abutment screw shoulder 225 is angled to conform to the angle of the abutment shoulder 160 of the abutment 100.

The abutment screw 200 has abutment screw threads 230 extending between a first and a second end 231 and 232. The abutment screw threads 230 are located in proximity to the second abutment screw end 202 of the abutment screw 200. The abutment screw threads 230 are selected to thread through the intermediate threads 170 of the abutment 100. The abutment screw threads 230 are selected to thread into the threaded portion 80 of the dental implant 10 to affix the abutment 100 to the dental implant 10.

An abutment screw bore 240 is defined in the first end 201 of the abutment screw 200. The abutment screw bore 240 comprises a lead in bore 240 extending between a first and a second end 241 and 242. The lead in bore 240 communicates an abutment screw socket 250 extending between a first and a second socket end 251 and 252. A relief 260 is located adjacent to the second socket end 252.

The abutment screw socket 250 is shown as a pentagonal socket 250 for receiving a conventional pentagonal key tool (not shown) for screwing the abutment screw 200 into the dental implant 10. The lead in bore 240 facilitates insertion of the conventional pentagonal keyed tool (not shown) into the abutment screw socket 250.

FIGS. 13-15 are various views of a healing cuff 300 suitable for use with dental implant 10 of FIG. 1. The healing cuff 300 extends between a top surface 301 and a lower surface 302. A tapered aperture 310 extends into the healing cuff 300 from the top surface 301. The tapered aperture 310 tapers from a large diameter 311 to a small diameter 312 defining a tapered shoulder 315.

The tapered aperture 310 communicates with a healing cuff bore 320. The healing cuff bore 320 extends between a first and a second end 321 and 322 and defines an annular shoulder 325. The healing cuff bore 320 is dimensioned to receive the cylindrical segment 30 of the dental implant 10.

A first and a second interproximal flat 331 and 332 are located on opposed sides on the healing cuff 300. The first and second interproximal flats 331 and 332 provide spaces between the healing cuff 300 and adjacent teeth or adjacent dental implants when implanted into a jaw bone of a patient.

FIGS. 16-18 are various views of a healing cuff screw 400 suitable for use with dental implant 10 of FIG. 1 and the healing cuff 300 of FIGS. 13-15. The healing cuff screw 400 extends between a first and a second healing cuff screw end 401 and 402.

The healing cuff screw 400 has a taper screw head 410 extending between a first taper end 411 and a second taper end 412. The taper screw head 410 tapers from a large diameter 411 to a small diameter 412 defining a tapered shoulder 415. The taper shoulder 415 is angled to coincide with the angle of the taper shoulder 315 defined in the healing cuff 300.

An upper healing cuff screw segment 420 extends between a first and a second end 421 and 422. The upper healing cuff screw segment 420 is located adjacent to the taper screw head 410. The upper healing cuff screw segment 420 is adapted to be received within the orientation portion 60 of the dental implant 10.

A lower healing cuff screw segment 430 extends between a first and a second end 431 and 432. The lower healing cuff screw segment 430 is adapted to be received within the counter bore 70 of the dental implant 10. A taper shoulder 435 is interposed between the upper healing cuff screw segment 420 and the lower healing cuff screw segment 430.

The healing cuff screw 400 has healing cuff screw threads 440 extending between a first and a second end 441 and 442. The healing cuff screw threads 440 are located in proximity to the second end 402 of the healing cuff screw 400. The healing cuff screw threads 440 are adapted to thread into the threaded portion 80 of the dental implant 10 to affix the healing cuff 300 to the dental implant 10. A taper shoulder 445 is interposed between the lower healing cuff screw segment 430 and the healing cuff screw threads 440.

A healing cuff screw bore 450 extends from the first end 401 of the healing cuff screw 400 into the interior of the healing cuff screw 400. A healing cuff screw socket 460 is defined within the healing cuff screw bore 450. The healing cuff screw socket 460 is shown as a hexagonal socket 460 for receiving a conventional hexagonal keyed tool (not shown) for screwing the healing cuff screw 400 into the dental implant 10.

Figure 19:
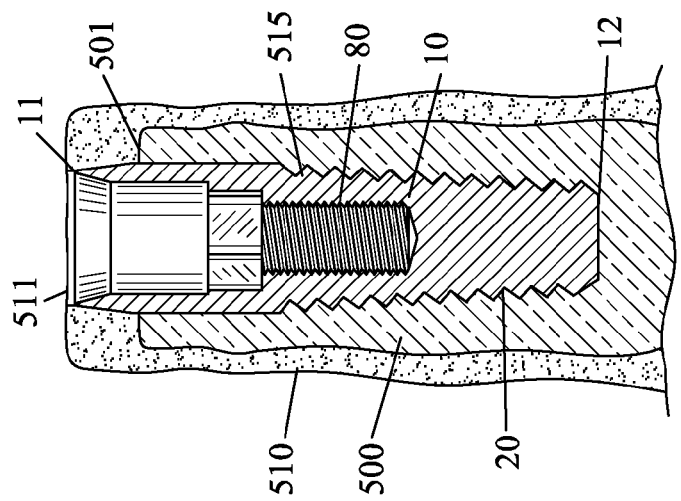
FIG. 19 is a side sectional view of the dental implant implanted within a jawbone of a patient.

FIG. 19 is a side sectional view of the dental implant 10 implanted within a jawbone 500 of a patient. Gum tissue 510 surrounds the jawbone 500 of the patient. An incision 511 is made in the crest of the gum tissue 510 at an edentulous location for providing access to the jawbone 500.

An osteotomy is formed by a drill (not shown) through the incision 511 for forming a void 515 within the jawbone 500. The dental implant 10 is inserted into the void 515 by twisting the dental implant 10 with a key tool (not shown) inserted within the orientation portion 60 of the dental implant 10. The cutouts 24 and 25 of the dental implant 10 provide a start for self tapping of the dental implant 10 into the jawbone 500.

Figure 20:
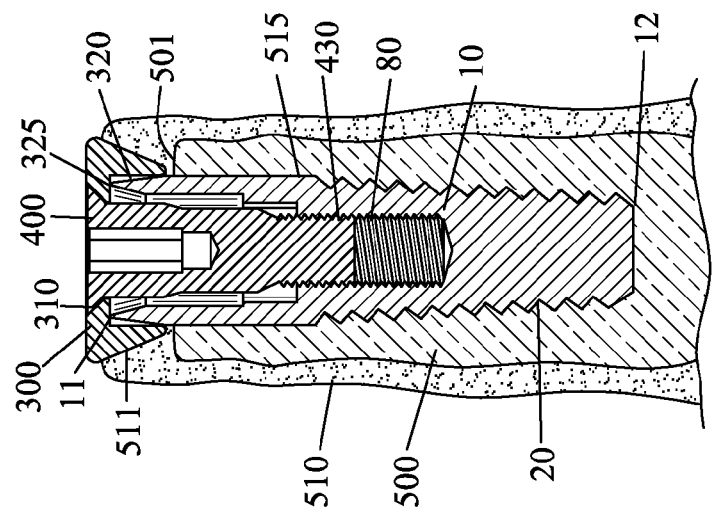
FIG. 20 is a side sectional view similar to FIG. 19 with the healing cuff secured to the dental implant.

FIG. 20 is a side sectional view similar to FIG. 19 with the healing cuff 300 secured to the dental implant 10 by the healing cuff screw 400. The healing cuff 300 is placed over the dental implant 10 such that the coronal end 11 is received within the healing cuff bore 320 of the healing cuff 300. The healing cuff screw 400 is passed through the taper aperture 310 and is threaded into the threaded portion 80 of the dental implant 10. The healing cuff screw 400 is tightened to bring the coronal end 11 of the dental implant 10 into engagement with the annular shoulder 325 of the healing cuff 300. Typically, the healing cuff 300 is kept on the dental implant 10 for a period of three to six months. After the threaded segment 20 of the dental implant 10 has become sufficiently osseointegrated, the healing cuff 300 is removed and the abutment 100 is secured to the dental implant 10.

Figure 21:
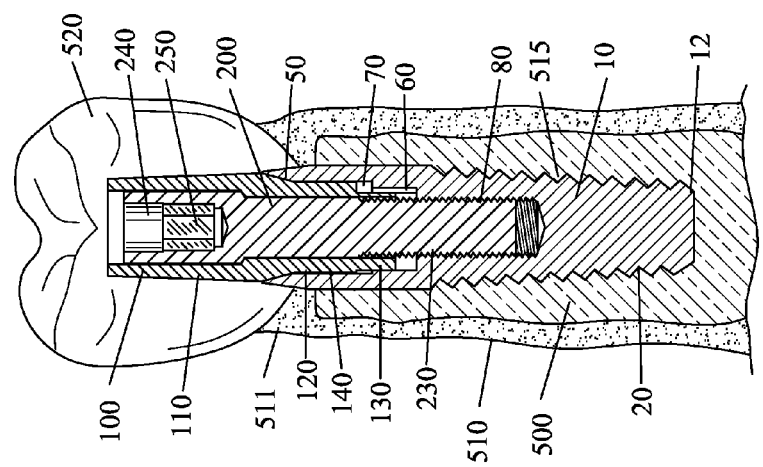
FIG. 21 is a side sectional view similar to FIG. 19 with the abutment secured to the dental implant.

FIG. 21 is a side sectional view similar to FIG. 20 with the abutment 100 secured to the dental implant 10 by the abutment screw 200. The abutment 100 is inserted into the orifice 40 of the dental implant 10. The orientation segment 130 of the abutment 100 is oriented relative to the orientation portion 60 of the dental implant 10 to properly position the abutment 100 relative to the dental implant 10.

The abutment screw 200 is inserted into the abutment bore 150. The abutment screw threads 230 are threaded through the intermediate threads 170 of the abutment 100. In some instances, it is desirable for temporarily affixing the abutment screw 200 to the abutment 100 prior to the insertion of the abutment 100 into the dental implant 10. In such instances, the abutment screw threads 230 are threaded through the intermediate threads 170 to maintain the abutment screw 200 within the abutment 100.

The abutment screw threads 230 of the abutment screw 200 are torqued into the threaded portion 80 enabling the shoulder 225 of the abutment screw 200 to engage with the shoulder 160 of the abutment 100 for securing the abutment 100 to the dental implant 10. The taper segment 120, the orientation segment 130 and the cylindrical segment 140 of the abutment 100 closely engage with the taper portion 50, the orientation portion 60 and the counter bore 70, respectively.

Figure 22:
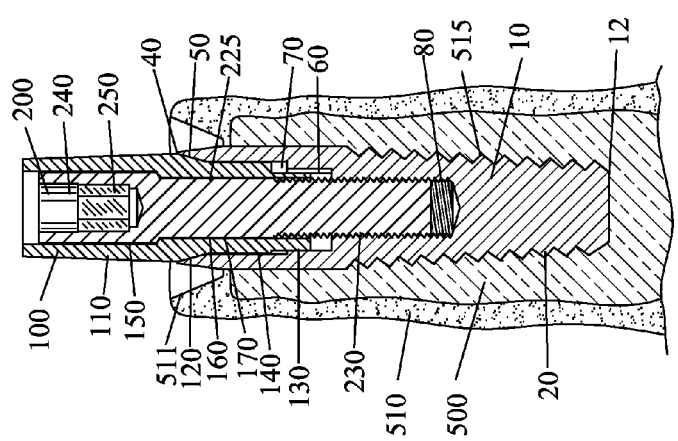
FIG. 22 is a side sectional view similar to FIG. 21 with a dental crown secured to the abutment of the dental implant.

FIG. 22 is a side sectional view similar to FIG. 21 with a dental crown 520 secured to the abutment 100 of the dental implant 10. Preferably, the abutment screw bore 240 including the abutment screw socket 250 is filled with a removable material in the remote events the abutment 100 requires removal in the future. The dental crown 520 is secured to the abutment 100 in a conventional fashion. In the alternative, the dental implant 10 and the abutment 100 may be used to provide a base for other dental prosthesis such as a dental bridge (not shown) or the like.

The following Table 1 presents representative examples of the dimensions of the dental implant 10 of the present invention but should not be construed as a limitation of the claimed invention.

TABLE 1

| Implant Length 11-12 | Orifice Length 41-42 | Taper Portion 51-52 | Orientation Portion 61-62 | Counter bore 71-72 | Threaded Portion 81-82 |
|---|---|---|---|---|---|
| 11 | 7.49 | 2.0 | 1.8 | 1.19 | 2.5 |
| 14 | 7.49 | 2.0 | 1.8 | 1.19 | 2.5 |
| 17 | 7.49 | 2.0 | 1.8 | 1.19 | 2.5 |
| 20 | 7.49 | 2.0 | 1.8 | 1.19 | 2.5 |

All dimensions are in millimeters.

Typically, the above dental implants 10 have diameters raging from 3.7 mm to 8.0 mm. The dental implants 10 may be provided with a pink coloration to reduce the possibility of the appearance of the dental implant 10 through the gum tissue of the patient.

The coloring of titanium and/or titanium alloys for dental implants provides optimum color matching to the gum tissue of the patient, added wear resistance and anti-galling properties. Preferably, the coloring of titanium and/or titanium alloys is the result of thin layer interference or iridescence of the oxide film formed on the surface of the dental implant 10 through a chemical or electrical process. The colors produced are similar to oil slicks, mother of pearl and soap bubbles, which are formed by the physical properties of light interference by the oxide film. There are no dyes or pigments used to produce colors; only oxygen. In order to produce color on titanium and titanium alloy implants, the thickness of the oxygen must be between 0.03 micro meters to 0.19 micro meters.

The dental implant 10 and the abutment 100 provide superior lateral or sheer strength to the dental crown 520. In the past, many abutments have failed due to lateral or sheer forces being applied to the dental crown. The present invention incorporates the counter bore 70 within the dental implant 10 cooperating with the cylindrical segment 140 within the abutment 100 for increasing the lateral stability of the abutment 100. In some examples of the dental implant 10, the length of the orifice 40 between the external orifice end 41 and the internal orifice end 42 being at least one-half of the distance between the coronal end 11 and the apical end 12 of the dental implant 10 provides increased lateral stability to the abutment 100.

FIG. 23 is a graph of force applied to a 3.7 mm dental implant 10 of the present invention as a function of time illustrating the strength of a dental implant 10. The 3.7 mm dental implant 10 exhibits no sign of failure to a test force of 1500 Newtons.

Figure 24:
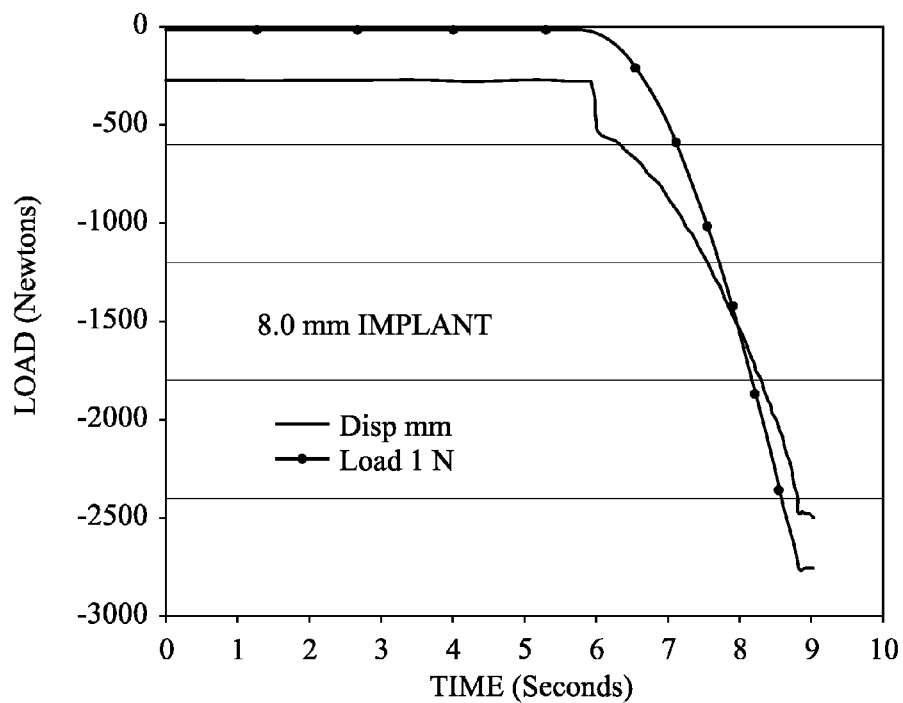
FIG. 24 is a graph of force applied to the dental implant of the present invention as a function of time illustrating the strength of an 8.0 mm dental implant.

FIG. 24 is a graph of force applied to a 8.0 mm dental implant 10 of the present invention as a function of time illustrating the strength of a dental implant 10. The 8.0 mm dental implant 10 exhibits no sign of failure to a test force of 2500 Newtons.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

FIGS. 25-28 are various views of a second embodiment of a dental implant 610 incorporating the present invention. Preferably, the dental implant 610 is used in concert with an abutment 700 shown in FIGS. 29-32, an abutment screw 800 shown in FIGS. 33-36. The dental implant 610 is suitable for use with the healing cuff 300 and healing cuff screw shown in FIGS. 13-18.

The dental implant 610 extends between a coronal end 611 and an apical end 612 defining an axis of symmetry 614. The dental implant 610 has an outer surface 615 reducing in diameter from the coronal end 611 to the apical end 612. The outer surface 615 of the dental implant 610 defines an outer thread segment 620 extending between a first end 621 and a second end 622. The outer thread segment 620 defines opposed cutouts 624 and 625 for providing a self tapping lead in for the thread segment 620.

The dental implant 610 has cylindrical segment 630 extending between a first and a second end 631 and 632 located in proximity to the coronal end 611. The cylindrical segment 630 comprises an upper cylindrical segment 634 and a lower cylindrical segment 635.

Fine pitch threads 637 are defined in the cylindrical segment 630 of the dental implant 610 adjacent to the second end 632 of the cylindrical segment 630. The fine pitch threads 637 are provided to engage with the crestal portion of the jawbone 500 of the patient Preferably, threaded segment 620 and the lower cylindrical segment 635 are treated with an abrasive material to provide a rough surface for adhering to a jawbone of a patient as will be described in greater detail hereinafter.

An orifice 640 extends into the dental implant 610 from an external orifice end 641 adjacent to the coronal end 611 toward an internal orifice end 642 in proximity to the apical end 612. The external end 641 adjacent to the coronal end 611 is an open end whereas the internal end 642 is a closed end.

A taper portion 650 is defined in the orifice 640 immediately adjacent to the coronal end 611. The taper portion 650 includes an inner taper portion 6501 and an external taper portion 650E. The inner taper portion 6501 extends between a first and a second taper end 651 and 652. In contrast the first embodiment of the dental implant 10 shown in FIGS. 1-22, the inner taper portion 6501 defines a taper angle of seven degrees relative to the axis of symmetry 614 extending through the dental implant 610.

The external taper portion 650E is defined in an outer surface of the cylindrical segment 630 adjacent to the first end 631. The external taper portion 650E extends between a first and a second taper end 656 and 657. In contrast the first embodiment of the dental implant 10 shown in FIGS. 1-22, the external taper portion 650E defines a taper angle of forty-five degrees relative to the axis of symmetry 614 extending through the dental implant 610.

The combination of the inner taper portion 6501 with a taper angle of approximately seven degrees and the external taper portion 650E with a taper angle of approximately forty-five degrees results in a thicker sidewall of the taper portion 650 contributing to an increase in strength of one hundred and fifty percent (150%) over the strength of the first embodiment of the dental implant 10 shown in FIGS. 1-22.

An orientation portion 660 is disposed in the orifice 640 located immediately adjacent to the taper portion 650 and in proximity to the coronal end 611 of the dental implant 610. The orientation portion 660 extends between a first and a second orientation end 661 and 662. A keyway 664 is defined in the orientation portion 660 for receiving a corresponding key defined in the abutment 700 for aligning the abutment 700 relative to the dental implant 610.

As best shown in FIG. 26, the keyway 664 is shown as a pentagon keyway defining a minimum radius 666 a maximum radius 668 relative to the axis of symmetry 614. The pentagon keyway 664 enables alignment of the abutment 700 in five different orientations relative to the dental implant 610. In addition, the keyway 664 provides a socket for receiving a conventional pentagon keyed tool (not shown) for screwing the dental implant 610 into the jaw bone of the patient.

A threaded portion 680 is disposed in the orifice 640 between the orientation portion 660 and the internal end 642 of the orifice 640. The threaded portion 680 extends between a first and a second end 681 and 682 defining threads 684. The threaded portion 680 receives a corresponding threaded portion of the abutment screw 800 for securing the abutment 700 to the dental implant 610.

In contrast to the first embodiment of the dental implant 10 shown in FIGS. 1-22, the orientation portion 660 is disposed between the taper portion 650 and a threaded portion 680. The second embodiment of the dental implant 610 extends the taper portion 650 into the region previously occupied by the counter bore 70 in the first embodiment of the dental implant 10.

In the first embodiment of the dental implant 10 as best shown in FIGS. 4 and 8, the counter bore 70 of the dental implant 10 has a radius sufficient to accommodate for the maximum radius 138 of the key 134 of the abutment 100. The radius of the counter bore 70 creates voids between the minimum radius 136 of the key 134 of the abutment 100 and the counter bore 70.

The extended orientation portion 660 of the dental implant 610 has two advantages over the counter bore 70 in the dental implant 10. Firstly, the increased length of the orientation portion 660 provides a stronger engagement with a keyed tool (not shown) for screwing the dental implant 610 into the jaw bone of the patient.

Secondly, the increased length of the orientation portion 660 provides a stronger sidewall of the orientation portion 660. The side wall of the extended orientation portion 660 of the dental implant 610 is thicker relative to the sidewall of the counter bore 70 in the dental implant 10.

Thirdly, the increased length of the orientation portion 660 eliminates the voids between the between the minimum radius 136 of the key 134 of the abutment 100 and the counter bore 70 found in the dental implant 10 and provides increased lateral stability to the abutment 700.

Figure 40:
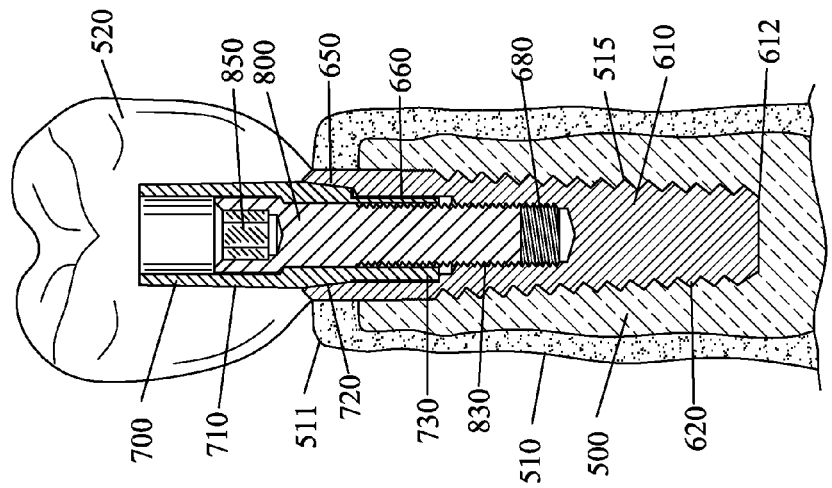
FIG. 40 is a side sectional view similar to FIG. 39 with a dental crown secured to the abutment of the dental implant;
Similar reference characters refer to similar parts throughout the several Figures of the drawings.

FIGS. 29-32 are various views of an abutment 700 suitable for use with dental implant 610 of FIG. 25. The abutment 700 extends between a first end 701 and a second end 702 along an axis of symmetry 704. The abutment 700 has mounting segment 710 extending between a first and a second end 711 and 712 located in proximity to the first end 701 of the abutment 700. The mounting segment 710 is adapted to receive a dental crown as shown in FIG. 40.

A taper segment 720 is located immediately adjacent to the mounting segment 710. The taper segment 720 extends between a first and a second taper end 721 and 722. The taper segment 720 defines a taper angle corresponding to the taper portion 650 disposed in the orifice 640 of the dental implant 610.

An orientation segment 730 is located immediately adjacent to the taper portion 720. The orientation segment 730 extends between a first and a second orientation end 731 and 732. A key 734 is defined in the orientation segment 730 for insertion into the corresponding keyway 664 defined in the dental implant 610 for aligning the abutment 700 relative to the dental implant 610.

As best shown in FIG. 31, the key 734 is shown as a pentagon key defining a minimum radius 736 a maximum radius 738 relative to the axis of symmetry 704. The pentagon key 734 enables alignment of the abutment 700 in five different orientations relative to the dental implant 610. No voids are created between the orientation portion 660 and the abutment 700 thus increasing lateral stability to the abutment 700.

An abutment bore 750 extends through the abutment 700 from a first bore end 751 and a second bore end 752. An abutment shoulder 760 extends into the abutment bore 750 intermediate the first and second bore ends 751 and 752. The abutment shoulder 760 is angles to connect the abutment bore 750 to intermediate threads 770. The intermediate threads 770 are disposed within the abutment bore 750 adjacent to the shoulder 760. The abutment bore 750 is adapted to receive the abutment screw 800 for securing the abutment 700 to the dental implant 610.

FIGS. 33-36 are various views of an abutment screw 800 suitable for use with dental implant 610 of FIGS. 25-28 and the abutment 700 of FIGS. 29-32. The abutment screw 800 extends between a first and a second abutment screw end 801 and 802.

The abutment screw 800 has an upper abutment screw segment 810 extending between a first and a second end 811 and 812 located in proximity to the first abutment screw end 801 of the abutment screw 800. The upper abutment screw segment 810 is adapted to be received within the abutment bore 750 of the abutment 700.

The abutment screw 800 has a lower abutment screw segment 820 extending between a first and a second end 821 and 822. An abutment screw shoulder 825 is interposed between the upper abutment screw segment 810 and the lower abutment screw segment 820. The abutment screw shoulder 825 is angled to conform to the angle of the abutment shoulder 760 of the abutment 700.

The abutment screw 800 has abutment screw threads 830 extending between a first and a second end 831 and 832. The abutment screw threads 830 are located in proximity to the second abutment screw end 802 of the abutment screw 800. The abutment screw threads 830 are selected to thread through the intermediate threads 770 of the abutment 700. The abutment screw threads 830 are selected to thread into the threaded portion 680 of the dental implant 610 to affix the abutment 700 to the dental implant 610.

An abutment screw bore 840 is defined in the first end 801 of the abutment screw 800. The abutment screw bore 840 comprises a lead in bore 840 extending between a first and a second end 841 and 842. The lead in bore 840 communicates an abutment screw socket 850 extending between a first and a second socket end 851 and 852. A relief 860 is located adjacent to the second socket end 852.

The abutment screw socket 850 is shown as a pentagonal socket 850 for receiving a conventional pentagonal key tool (not shown) for screwing the abutment screw 800 into the dental implant 610. The lead in bore 840 facilitates insertion of the conventional pentagonal keyed tool (not shown) into the abutment screw socket 850.

The second embodiment of the dental implant 610 of FIG. 25 is compatible for use with the healing cuff 300 shown in FIGS. 13-15 as well as the healing cuff screw 400 shown in FIGS. 16-18.

Figure 37:
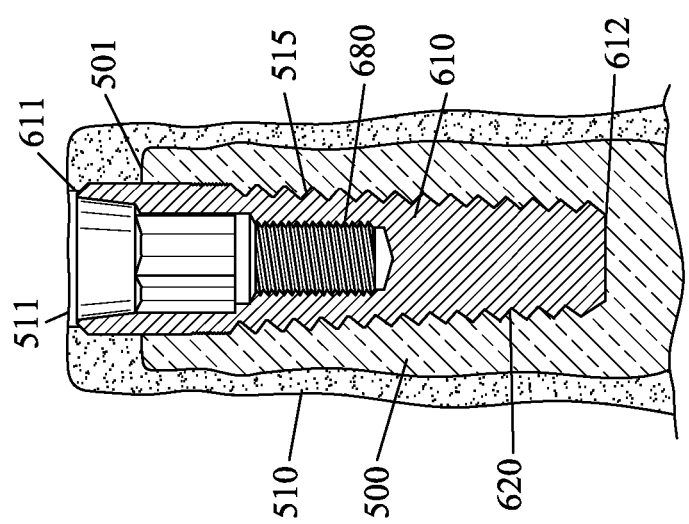
FIG. 37 is a side sectional view of the second embodiment of the dental implant implanted within a jawbone of a patient.

FIG. 37 is a side sectional view of the dental implant 610 implanted within a jawbone 500 of a patient. Gum tissue 510 surrounds the jawbone 500 of the patient. An incision 511 is made in the crest of the gum tissue 510 at an edentulous location for providing access to the jawbone 500.

An osteolomy is formed by a drill (not shown) through the incision 511 for forming a void 515 within the jawbone 500. The dental implant 610 is inserted into the void 515 by twisting the dental implant 610 with a key tool (not shown) inserted within the orientation portion 660 of the dental implant 610. The fine pitch threads 637 of the dental implant 610 engage with the crestal portion of the jawbone 500 of the patient to promote initial bonding the dental implant 610.

Figure 38:
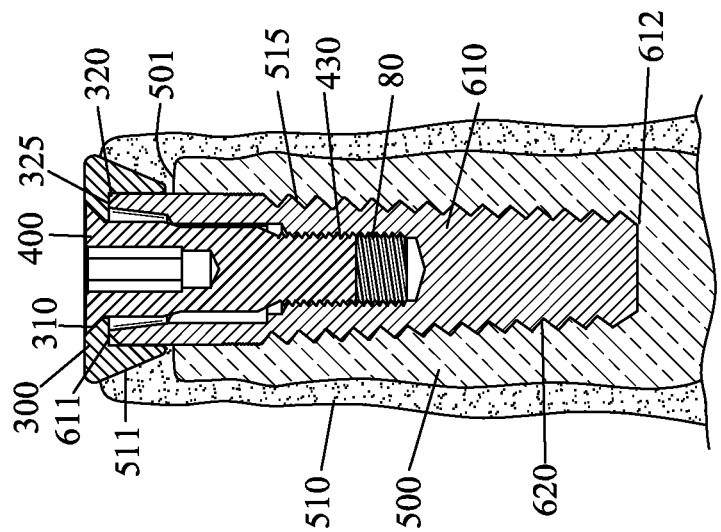
FIG. 38 is a side sectional view similar to FIG. 37 with the healing cuff secured to the dental implant.

FIG. 38 is a side sectional view similar to FIG. 37 with the healing cuff 300 secured to the dental implant 610 by the healing cuff screw 400. The healing cuff 300 is placed over the dental implant 610 such that the coronal end 611 is received within the healing cuff bore 320 of the healing cuff 300. The healing cuff screw 400 is passed through the taper aperture 310 and is threaded into the threaded portion 680 of the dental implant 610.

Figure 39:
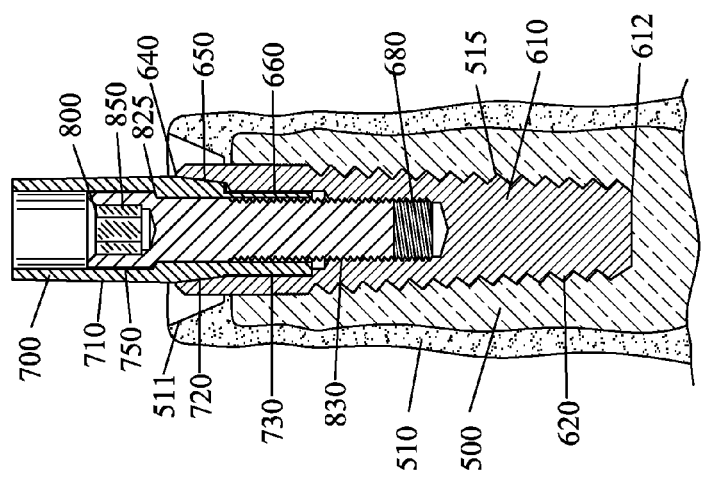
FIG. 39 is a side sectional view similar to FIG. 37 with the abutment secured to the dental implant.

FIG. 39 is a side sectional view similar to FIG. 37 with the abutment 700 secured to the dental implant 610 by the abutment screw 800. The orientation segment 730 of the abutment 700 is oriented relative to the orientation portion 660 of the dental implant 610 to properly position the abutment 700 relative to the dental implant 610. The abutment screw 800 is inserted into the abutment bore 150.

The taper segment 720 of the abutment 700 closely engages with the taper portion 650 of the dental implant 610. In addition the orientation segment 730 of the abutment 700 closely engages with the orientation portion 660 of the dental implant 610 without any voids therebetween.

FIG. 40 is a side sectional view similar to FIG. 39 with a dental crown 520 secured to the abutment 700 of the dental implant 610. The dental crown 520 is secured to the abutment 700 in a conventional fashion. In the alternative, the dental implant 610 and the abutment 700 may be used to provide a base for other dental prosthesis such as a dental bridge (not shown) or the like.

The following Table 2 presents representative examples of the dimensions of the dental implant 610 of the present invention but should not be construed as a limitation of the claimed invention.

TABLE 2

| Implant Length 611-612 | Orifice Length 641-642 | Taper Portion 651-652 | Orientation Portion 661-662 | Threaded Portion 681-682 |
| --- | --- | --- | --- | --- |
| 11 | 8.1 | 1.6 | 3.0 | 3.5 |
| 14 | 8.1 | 1.6 | 3.0 | 3.5 |
| 17 | 8.1 | 1.6 | 3.0 | 3.5 |
| 20 | 8.1 | 1.6 | 3.0 | 3.5 |

All dimensions are in millimeters.

FIG. 23 is a graph of force applied to a 3.7 mm dental implant 10 of the first embodiment of the present invention shown in FIGS. 1-22 as a function of time illustrating the strength of a dental implant 10. The 3.7 mm dental implant 10 exhibits no sign of failure to a test force of 1500 Newtons.

The dental implant 610 of the second embodiment of the invention shown in FIGS. 25-40 exhibits an increase in strength of one hundred and fifty percent (150%) over the strength of the first embodiment of the dental implant 10 shown in FIGS. 1-22. The 3.7 mm dental implant 610 exhibits no sign of failure to a test force of 2250 Newtons.

FIG. 24 is a graph of force applied to a 8.0 mm dental implant 10 of the present invention as a function of time illustrating the strength of a dental implant 10. The 8.0 mm dental implant 10 exhibits no sign of failure to a test force of 2500 Newtons.

The dental implant 610 of the second embodiment of the invention shown in FIGS. 25-40 exhibits an increase in strength of one hundred and fifty percent (150%) over the strength of the first embodiment of the dental implant 10 shown in FIGS. 1-22. The 8.0 mm dental implant 610 exhibits no sign of failure to a test force of 10,000 Newtons.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An improved dental prosthesis for implanting into a jawbone of a patient, comprising:
   a dental implant having a coronal end and a small apical end;
   an orifice extending into said dental implant from an external orifice end adjacent to said coronal end toward an internal orifice end in proximity to said apical end;
   a threaded portion disposed in said orifice located adjacent to said internal e of said orifice;
   an orientation portion disposed in said orifice located in proximity to said coronal end of said dental implant;
   an abutment having a key;
   a keyway defined in said orientation portion for receiving said key in said abutment for aligning said abutment relative to said dental implant;
   a threaded screw engaging with said threaded portion in said orifice for securing said abutment to said dental implant;
   an external taper portion immediately adjacent to said coronal end of said dental implant; and
   a dental crown engaging both said abutment and said external taper portion of said dental implant for increasing the lateral stability of said dental crown.

2. An improved dental prosthesis as set forth in claim 1, wherein said dental implant has an outer surface reducing in diameter from said coronal end to said apical end; and
   said outer surface of said dental implant defining outer threads for affixing said dental implant to the jawbone of a patient.

3. An improved dental prosthesis as set forth in claim 1, wherein said external end adjacent to said coronal end is an open end and said internal end in proximity to said apical end is a closed end.

4. An improved dental prosthesis as set forth in claim 1, including a taper portion defined in said orifice immediately adjacent to said coronal end.

5. An improved dental prosthesis as set forth in claim 1, including an inner taper portion defined in said orifice immediately adjacent to said coronal end; and
   said inner taper portion defining a taper angle of approximately seven degrees relative to an axis of symmetry extending through said dental implant.

6. An improved dental prosthesis as set forth in claim 1, wherein
   said external taper portion defining a taper angle of approximately forty-five degrees relative to an axis of symmetry extending through said dental implant.

7. An improved dental prosthesis as set forth in claim 1, wherein said keyway includes a pentagonal keyway for receiving a pentagonal keyed tool for screwing said dental implant into the jaw bone of the patient.

8. An improved dental prosthesis as set forth in claim 1, wherein said keyway includes a pentagonal keyway for aligning said abutment relative to said dental implant.

9. An improved dental prosthesis as set forth in claim 1, including a counter bore disposed in said orifice and interposed between said orientation portion and said threaded portion for providing increased lateral stability to said abutment.

10. An improved dental prosthesis as set forth in claim 1, including a counter bore disposed in said orifice and interposed between said orientation portion and said threaded portion for providing increased lateral stability to said abutment; and
said counter bore defining a cylindrical counter bore for receiving a cylindrical portion of said abutment.

11. An improved dental prosthesis as set forth in claim 1, including a counter bore disposed in said orifice and interposed between said orientation portion and said threaded portion for providing increased lateral stability to said abutment;
said counter bore defines a cylindrical counter bore for receiving a cylindrical portion of said abutment; and
said cylindrical counter bore having a diameter greater that the diameter of said threaded portion.

12. An improved dental prosthesis as set forth in claim 1, including a counter bore disposed in said orifice and interposed between said orientation portion and said threaded portion for providing increased lateral stability to said abutment;
said keyway defines a minimum radius and a maximum radius; and
said cylindrical counter bore having a diameter commensurate with said maximum radius of said keyway.

13. An improved dental prosthesis as set forth in claim 1, further including a healing cuff temporality engaging said dental implant; and
a healing cuff screw traversing said healing cuff and threadably engaging said dental implant.

14. An improved dental prosthesis as set forth in claim 1, wherein said dental implant includes a cylindrical segment extending between a first end a second end in proximity to said coronal end;
a fine pitch thread adjacent to said second end of said cylindrical segment for engaging a portion of the jawbone.

15. An improved dental prosthesis for implanting into a jawbone of a patient, gun tissue covering a portion of the jawbone, the improved dental prosthesis, comprising:
a dental implant having a coronal end and a small apical end;
an orifice extending into said dental implant from an external orifice end adjacent to said coronal end toward an internal orifice end in proximity to said apical end;
a threaded portion disposed in said orifice located adjacent to said internal end of said orifice;
all orientation portion disposed in said orifice located in proximity to said coronal end of said dental implant;
an abutment having a key;
a keyway defined in said orientation portion for receiving said key in said abutment for aligning said abutment relative to said dental implant;
a threaded screw engaging with said threaded portion in said orifice for securing said abutment to said dental implant; and
said dental implant including a pink coloration for reducing the appearance of said dental implant through the gum tissue of the patient.

16. An improved dental prosthesis for implanting into a jawbone of a patient, gun tissue covering a portion of the jawbone, the improved dental prosthesis, comprising:
a dental implant having a coronal end and a small apical end;
an orifice extending into said dental implant from an external orifice end adjacent to said coronal end toward an internal orifice end in proximity to said apical end;
a threaded portion disposed in said orifice located adjacent to said internal end of said orifice;
an orientation portion disposed in said orifice located in proximity to said coronal end of said dental implant;
an abutment having a key;
a keyway defined in said orientation portion for receiving said key in said Abutment for aligning said abutment relative to said dental implant;
a threaded screw engaging with said threaded portion in said orifice for securing said abutment to said dental implant;
an external taper portion immediately adjacent to said coronal end of said dental implant;
a dental crown engaging both said abutment and said external taper portion of said dental implant for increasing the lateral stability of said dental crown; and
said dental implant including a pink coloration for reducing the appearance of said dental implant through the gum tissue of the patient.

* * * * *